United States Patent
Wu et al.

(10) Patent No.: US 8,067,452 B2
(45) Date of Patent: Nov. 29, 2011

(54) 3-HYDROXYISOTHIAZOLE-4-CARBOXAMIDINE DERIVATIVES AS CHK2 INHIBITORS

(75) Inventors: Jim Zhen Wu, Shanghai (CN); Huanming Chen, Irvine, CA (US)

(73) Assignee: Valeant Pharmaceuticals International, Aliso Viejo, CA (US)

( * ) Notice: Subject to any disclaimer, the term of this patent is extended or adjusted under 35 U.S.C. 154(b) by 322 days.

(21) Appl. No.: 12/143,672

(22) Filed: Jun. 20, 2008

(65) Prior Publication Data

US 2009/0137041 A1    May 28, 2009

Related U.S. Application Data

(60) Provisional application No. 60/936,720, filed on Jun. 21, 2007.

(51) Int. Cl.
*A61K 31/425* (2006.01)
*C07D 275/03* (2006.01)
(52) U.S. Cl. ........................ 514/372; 548/213
(58) Field of Classification Search ............... 514/372; 548/213
See application file for complete search history.

(56) References Cited

U.S. PATENT DOCUMENTS

| 7,429,667 B2 * | 9/2008 | Abdellaoui et al. | 548/213 |
| 7,652,047 B2 * | 1/2010 | Abdellaoui et al. | 514/372 |

OTHER PUBLICATIONS

El Abdellaoui et al. Bioorganic & Medicinal Chem. Lett. 2006, 16(21), 5561-66.*
Carlessi et al. Molecular Cancer Therapeutics 2007, 6(3), 935-44.*
Larson, et al., "Identification of novel, selective and potent Chk2 inhibitors," *Bioorganic & Med. Chem Ltrs* 12:172-175 (2007).

* cited by examiner

*Primary Examiner* — Jason M Nolan
(74) *Attorney, Agent, or Firm* — Jones Day

(57) ABSTRACT

This invention provides compounds of Formula I which are inhibitors of Chk2 and are useful as a radiation protection agents in anticancer radiotherapy. A method of modulating Chk2 in vitro includes treating a substrate with Chk2 in the presence of compounds of formula I. A method of making a compound of formula I includes: a) forming a biaryl amine having an amino ($NH_2$) group; b) converting the amino group to an isothiocyanate group; c) adding a cyanoacetamide to the isothiocyanate group to form a thioamide adduct; d) cyclizing the thioamide adduct to form an isothiazole having a cyano group; and e) adding an amine to the cyano group to form a carboxamidine group.

9 Claims, No Drawings

3-HYDROXYISOTHIAZOLE-4-CARBOXAMIDINE DERIVATIVES AS CHK2 INHIBITORS

CROSS-REFERENCE TO RELATED APPLICATIONS

This application claims the benefit of priority of U.S. Provisional No. 60/936,720, filed Jun. 21, 2007, the entire contents of which is incorporated herein by this reference.

BACKGROUND

This invention concerns novel compounds that act as selective inhibitors for Chk2. The compounds possess the cellular activity to regulate the Chk2-mediated cell cycle arrest and apoptosis. They are potentially useful as radiation protection agents in anticancer radiotherapy.

The maintenance of an intact genome is of crucial importance to every organism. Each individual cell in a multicellular eukaryotic organism possesses sophisticated and intricate mechanisms to properly respond to DNA damage. Such mechanisms repair damaged DNA or trigger programmed cell death (apoptosis). Checkpoint kinases are thought to be intimately involved in these processes.

Checkpoint Kinase 2 ("Chk2") is one of the major effectors of the replication checkpoint. The crucial roles played by Chk2 in mediating cellular responses to DNA damage implicate its potential value in cancer therapies. The inhibition of Chk2 could protect normal cells from the effects of ionizing radiation or DNA-damaging chemotherapeutics while increasing the cancer cells' susceptibility to such treatments, thus enhancing both the efficacy and the safety of such therapies.

SUMMARY OF THE INVENTION

The present invention is directed to compounds of formula I,

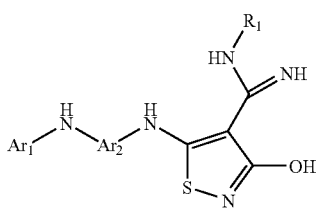

where $Ar_1$ and $Ar_2$ are, independently, phenyl, or pyridyl, in which $Ar^1$ is optionally substituted with substituents $R_2$ and $R_3$ which are selected independently from hydrogen; halogen; hydroxy; nitro; cyano; $C_1$-$C_4$ alkyl; $OC_1$-$C_4$ alkyl, where the $C_1$-$C_4$ alkyl groups and the $C_1$-$C_4$ alkyl moieties of the $OC_1$—Ca alkyl groups are optionally substituted with one to three fluorine atoms; $NR_6R_7$, $(CH_3)_2N$; $CH_3OC(O)$; $CH_3CH_2OC(O)$; —$C(O)NR_6R_7$; or —$S(O)_2NR_6R_7$, where $R_6$ and $R_7$ are, independently, H, $CH_3$, or $CH_3CH_2$; or $R_2$ and $R_3$ are attached to adjacent carbons and, together with the ring atoms to which they are attached, form an additional, fused, five- or six-membered ring, optionally containing one heteroatom, which ring may be aromatic or aliphatic;

$Ar_2$ is optionally substituted with substituents $R_4$ and $R_5$ which are selected independently from H, F, Cl, Br, $CH_3$, or $CF_3$;

and $R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1C_3$ alkoxy, and phenyl; or $R_1$ is —$CH_2B$ or —$CH_2CH_2B$, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or $R_i$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$—Ca alkyl, wherein said $C_1$—Ca alkyl group is optionally substituted with one to three halogen atoms; and wherein each ring optionally contains one or more double bonds;

or $R_1$ is —$CH(CH_2OH)CH_2D$, where D is selected from imidazolyl, indolyl, carboxamido, phenyl, cyclohexyl, —$CH_2SCH_3$, and adamantin-1-yl; or all tautomers, pharmaceutically acceptable salts and stereoisomeric forms thereof. Such compounds are selective inhibitors for Chk2.

In another aspect the present invention is directed to compounds of formula II,

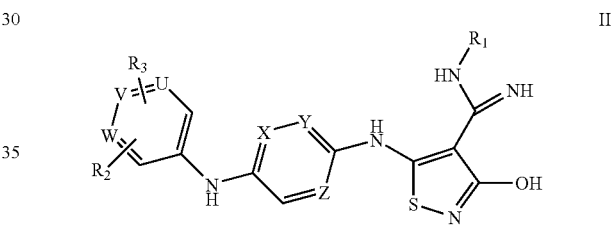

in which U, V, W, X, Y, and Z are, independently CH, C—$CH_3$, or N, provided that no two adjacent ring atoms are N; and in which substituents $R_1$-$R_3$ are as defined in formula I.

In still another aspect the present invention is directed to compounds of formula III:

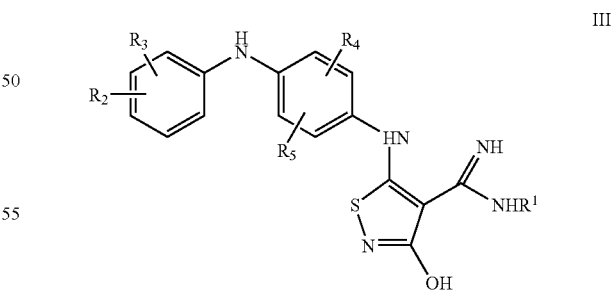

wherein
$R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_1$ is —$CH_2B$ or —$CH_2CH_2B$, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or $R_1$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;

or $R_1$ is —CH(CH$_2$OH)CH$_2$D, where D is selected from imidazolyl, indolyl, carboxamido, phenyl, cyclohexyl, —CH$_2$SCH$_3$, and adamantin-1-yl; and $R_2$ and $R_3$ vary independently and are selected from the group consisting of hydrogen; halogen; hydroxy; nitro; cyano; $C_1$-$C_4$ alkyl; OC$_1$-$C_4$ alkyl, where the $C_1$-$C_4$ alkyl groups and the $C_1$-$C_4$ alkyl moieties of the OC$_1$-$C_4$ alkyl groups are optionally substituted with one to three fluorine atoms; NR$_6$R$_7$, (CH$_3$)$_2$N; CH$_3$OC(O); CH$_3$CH$_2$OC(O); —C(O)NR$_6$R$_7$; or —S(O)$_2$NR$_6$R$_7$, where R$_6$ and R$_7$ are, independently, H, CH$_3$, or CH$_3$CH$_2$; or R$_2$ and R$_3$ are attached to adjacent carbons and, together with the ring atoms to which they are attached, form an additional, fused, five- or six-membered ring, optionally containing one heteroatom, which ring may be aromatic or aliphatic; and $R_4$ and $R_5$ vary independently and are selected from the group consisting of H, F, Cl, Br, CH$_3$, or CF$_3$.

In yet another aspect the present invention is directed to compounds of formula IV:

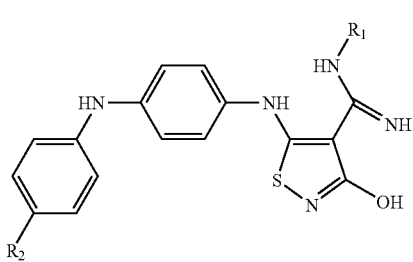

wherein
$R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_1$ is —CH$_2$B or —CH$_2$CH$_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or $R_1$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;

or $R_1$ is —CH(CH$_2$OH)CH$_2$D, where D is selected from imidazolyl, indolyl, carboxamido, phenyl, cyclohexyl, —CH$_2$SCH$_3$, and adamantin-1-yl; and $R_2$ is selected from the group consisting of hydrogen or halogen.

In still further aspects, embodiments disclosed here relate to a method of modulating Chk2 in vitro. The method includes treating a substrate with Chk2 in the presence of a compound of formulas I-IV.

In yet still further aspects, embodiments disclosed herein relate to a method of making a compounds of formulas III and IV. The method includes: a) forming a biaryl amine having an amino (NH$_2$) group; b) converting the amino group to an isothiocyanate group; c) adding a cyanoacetamide to the isothiocyanate group to form a thioamide adduct; d) cyclizing the thioamide adduct to form an isothiazole having a cyano group; and e) adding an amine to the cyano group to form a carboxamidine group.

DETAILED DESCRIPTION

In one embodiment, this invention provides compounds of formula I,

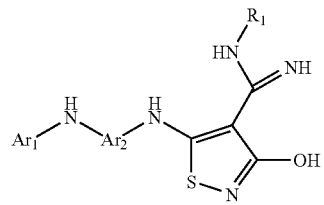

where Ar$_1$ and Ar$_2$ are, independently, phenyl, or pyridyl, in which Ar$_i$ is optionally substituted with substituents R$_2$ and R$_3$ which are selected independently from hydrogen; halogen; hydroxy; nitro; cyano; $C_1$-$C_4$ alkyl; OC$_1$-$C_4$ alkyl, where the $C_1$-$C_4$ alkyl groups and the $C_1$-$C_4$ alkyl moieties of the OC$_1$-$C_4$ alkyl groups are optionally substituted with one to three fluorine atoms; NR$_6$R$_7$, (CH$_3$)$_2$N; CH3OC(O); CH$_3$CH$_2$OC(O); —C(O)NR$_6$R$_7$; or —S(O)$_2$NR$_6$R$_7$, where R$_6$ and R$_7$ are, independently, H, CH$_3$, or CH$_3$CH$_2$; or R$_2$ and R$_3$ are attached to adjacent carbons and, together with the ring atoms to which they are attached, form an additional, fused, five- or six-membered ring, optionally containing one heteroatom, which ring may be aromatic or aliphatic;

Ar$_2$ is optionally substituted with substituents R$_4$ and R$_5$ which are selected independently from H, F, Cl, Br, CH$_3$, or CF$_3$;

and $R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_3$ alkoxy, and phenyl; or $R_1$ is —CH$_2$B or —CH$_2$CH$_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or $R_1$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;

or $R_1$ is —CH($CH_2$OH)$CH_2$D, where D is selected from imidazolyl, indolyl, carboxamido, phenyl, cyclohexyl, —$CH_2SCH_3$, and adamantin-1-yl; or all tautomers, pharmaceutically acceptable salts and stereoisomeric forms thereof. Such compounds are selective inhibitors for Chk2.

In one subgeneric embodiment, the invention provides a compound of formula II below

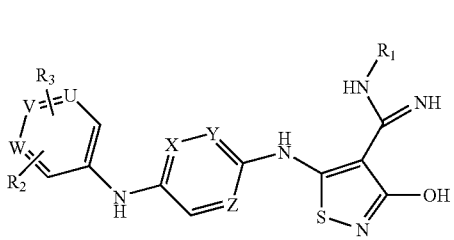

II in which U, V, W, X, Y, and Z are, independently CH, C—$CH_3$, or N, provided that no two adjacent ring atoms are N; and in which substituents $R_1$-$R_3$ are as defined in formula I.

In a more specific subgeneric embodiment, this invention provides a compound of formula III below:

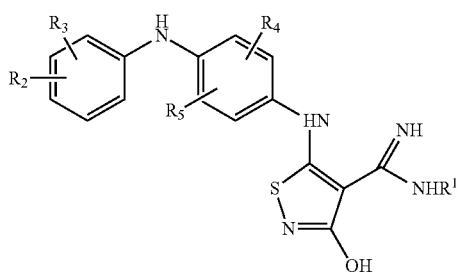

III wherein
$R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_1$ is —$CH_2$B or —$CH_2CH_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;
or $R_1$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;
or $R_1$ is —CH($CH_2$OH)$CH_2$D, where D is selected from imidazolyl, indolyl, carboxamido, phenyl, cyclohexyl, —$CH_2SCH_3$, and adamantin-1-yl; and $R_2$ and $R_3$ vary independently and are selected from the group consisting of hydrogen; halogen; hydroxy; nitro; cyano; $C_1$-$C_4$ alkyl; O$C_1$-$C_4$ alkyl, where the $C_1$-$C_4$ alkyl groups and the $C_1$-$C_4$ alkyl moieties of the O$C_1$-$C_4$ alkyl groups are optionally substituted with one to three fluorine atoms; $NR_6R_7$, $(CH_3)_2N$; $CH_3$OC(O); $CH_3CH_2$OC(O); —C(O)$NR_6R_7$; or —S(O)$_2NR_6R_7$, where $R_6$ and $R_7$ are, independently, H, $CH_3$, or $CH_3CH_2$; or $R_2$ and $R_3$ are attached to adjacent carbons and, together with the ring atoms to which they are attached, form an additional, fused, five- or six-membered ring, optionally containing one heteroatom, which ring may be aromatic or aliphatic;

$R_4$ and $R_5$ vary independently and are selected from the group consisting of H, F, Cl, Br, $CH_3$, or $CF_3$;
and salts thereof.

In a still further specific subgeneric embodiment, this invention provides compounds of formula IV:

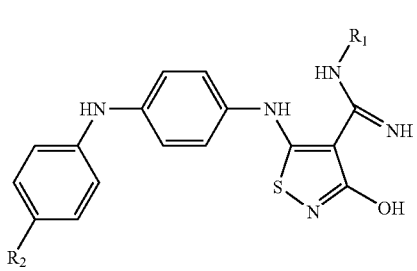

IV wherein
$R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_1$ is —$CH_2$B or —$CH_2CH_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;
or $R_1$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;
or $R_1$ is —CH($CH_2$OH)$CH_2$D, where D is selected from imidazolyl, indolyl, carboxamido, phenyl, cyclohexyl, —$CH_2SCH_3$, and adamantin-1-yl;
$R_2$ is selected from the group consisting of hydrogen or halogen;
and salts thereof.

In another more specific subgeneric embodiment, this invention provides a compound of formula III in which $R_2$ and $R_3$ are, independently, H, methyl, halogen. $CF_3$, or methoxy.

In another more specific subgeneric embodiment, this invention provides a compound of formula III in which $R_1$ is $C_1$-$C_4$ alkyl, optionally substituted with one or two OH groups.

In another more specific subgeneric embodiment, this invention provides a compound of formula III in which $R_1$ is $(CH_2)_n$G.

In another more specific subgeneric embodiment, this invention provides a compound of formula III in which $R_1$ is $(CH_2)_n$-G wherein G is phenyl, naphthyl, cyclopentyl, or cyclohexyl.

In another more specific subgeneric embodiment, this invention provides a compound of formula III in which $R_1$ is $C_1$-$C_4$ alkyl, optionally substituted with one or two OH groups, and $R_3$, $R_4$, and $R_5$ are H and $R_2$ is H or halogen.

In another more specific subgeneric embodiment, this invention provides a compound of formula III in which $R_1$ is ($C^H$ArG, $R_3$, Ra, and $R_5$ are H, and $R_2$ is H or halogen.

In another more specific subgeneric embodiment, this invention provides a compound of formula III in which $R_1$ is $(CH_2)_n$-G, in which G is phenyl, naphthyl, cyclopentyl, or cyclohexyl, and $R_3$, $R_4$, and $R_5$ are H and $R_2$ is H or halogen.

In another embodiment, this invention provides a composition comprising a pharmaceutically acceptable carrier and at least one of the following: i) a pharmaceutically effective amount of a compound of formulas I, II, III or IV and ii) a pharmaceutically acceptable salt, ester, or prodrug thereof.

In yet another embodiment, this invention provides a method of enhancing the efficacy of anticancer radiotherapy by the inhibition of Chk2, comprising administering to a patient in need thereof a therapeutically effective amount of a compound of formulas I, II, III, or IV or a salt, ester, or prodrug thereof.

The examples below are intended to illustrate, but not to limit, the range of compounds contemplated by this invention.

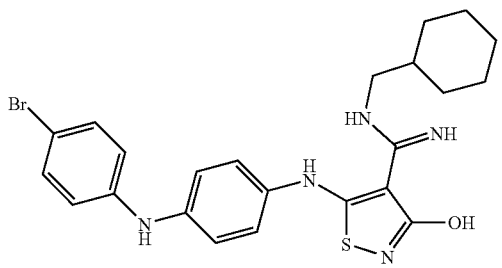

1

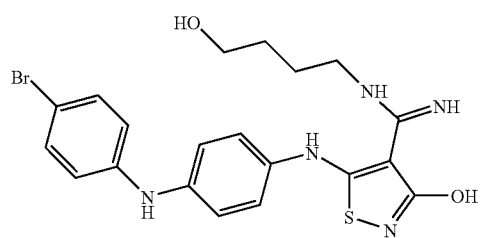

2

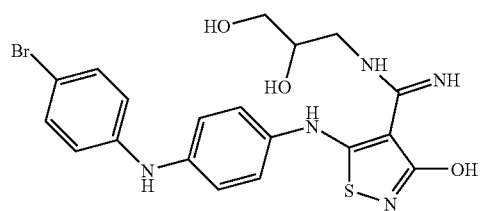

3

-continued

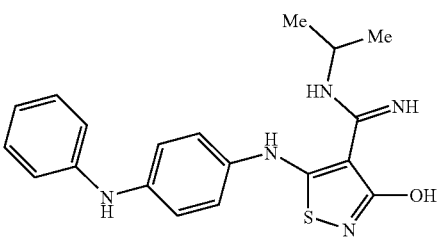

4

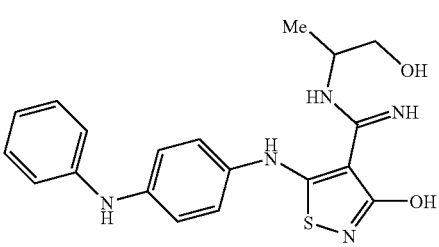

5

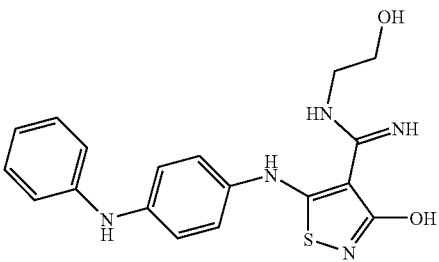

6

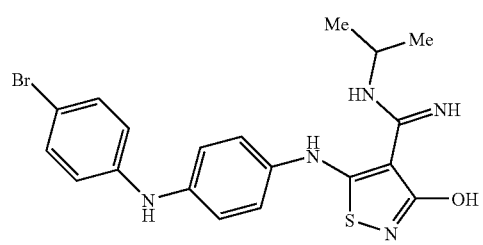

7

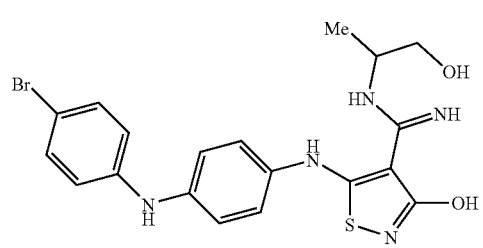

8

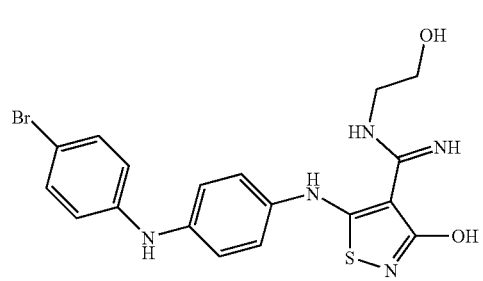

9

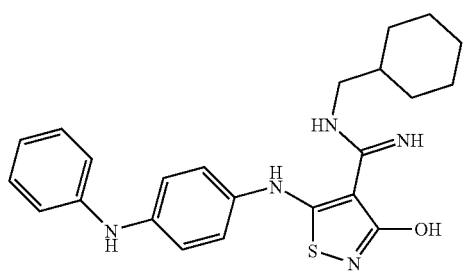
10
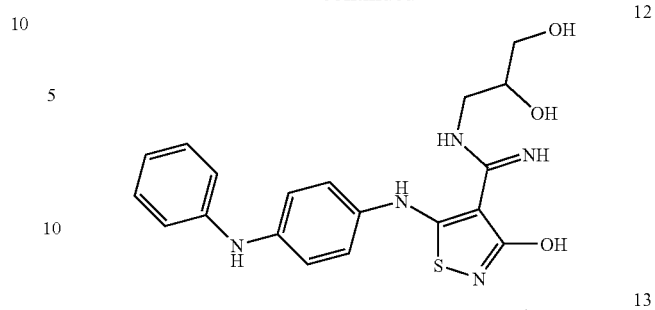
12
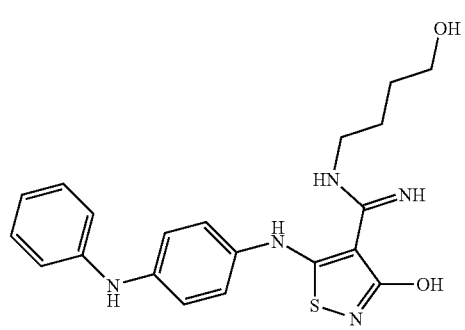
11
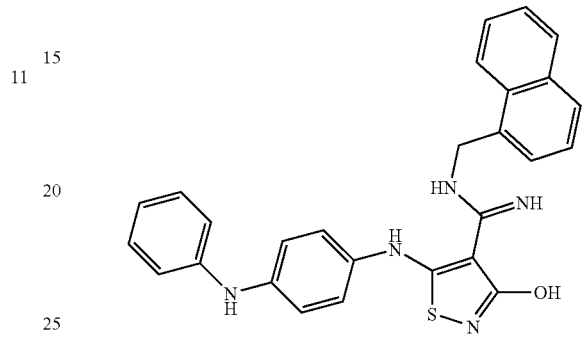
13
Preparation of Compounds
The preparation of compounds of 5-[4-(phenylamino)-phenylamino]-3-hydroxy-isothiazole-4-carboxamidine derivatives is outlined in Scheme 1:
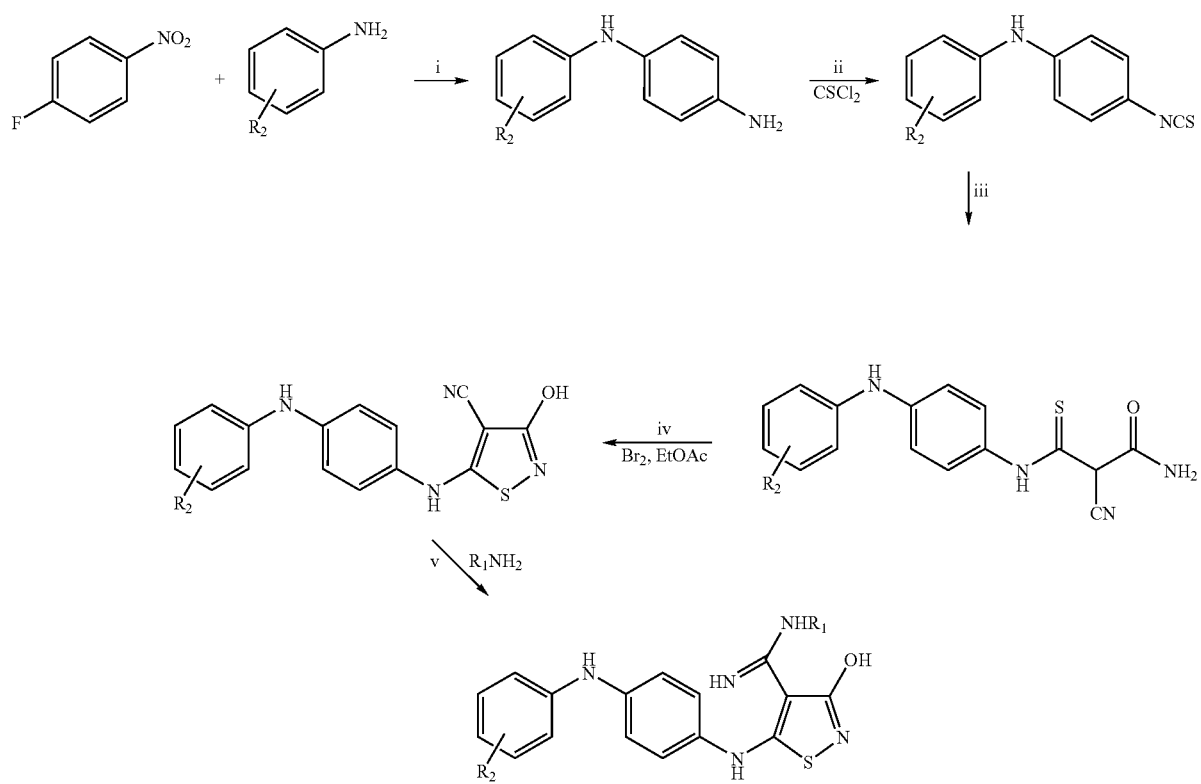

Procedures (Step i)

A mixture of 4-fluoronitrobenzene (0.02 mol), anilines (0.022 mol), and potassium carbonate (0.022 mol) in 40 ml of anhydrous DMF was heated to 150° C. with stirring for overnight. After cooling to room temperature, the reaction mixture was poured into 500 ml of ice water and stirred for 30 min. The precipitates formed were collected by filtration, washed with water and dried in vacuo to give the intermediate. This crude intermediate was dissolved in 100-200 ml of ethanol, and 1-2 g 10% Pd—C was added. The compound was hydrogenated under ambient pressure at room temperature for 5-6 hours. Then the catalyst was removed by filtration, and the filtrate was concentrated to dryness to give a mixture of crude anilines, which was used for the next step with further purification.

Procedures (Step ii)

To a solution of aniline (30 mmol) and DBU (60 mmol) in 60 ml of anhydrous dichloromethane, a solution of thiophosgene (30 mmol) in 20 ml of dry dichloromethane was added dropwise with stirring at room temperature. Addition was complete after 30 min. The reaction mixture was diluted with 200 ml of chloroform and washed with 1N HCl solution (300 ml×2) and water. The chloroform solution was dried over anhydrous sodium sulfate and the solvent was evaporated in vacuo. The residue was purified by silica gel column to give pure isothiocyanates.

Procedures (Step iii)

To a solution of potassium tert-butyloxide (20 mmol) in 20 ml of anhydrous THF was added 2-cyanoacetamide (20 mmol), then this mixture was cooled to 5° C. and added dropwise a solution of isothiocyanates (20 mmol) in 5 ml of dry THF with stirring under argon. After 15 min with stirring at 5° C., this reaction mixture was warmed to room temperature and stirred for another 1 h. The reaction mixture was poured into 1000 ml of ice water and neutralized with 2% HCl to pH<7. The solid was filtered and washed with water. After drying in vacuo, the crude product was obtained and used without further purification for the next step. Yield: 72-97%

General Procedures (Step iv)

To a solution or suspension of the product obtained from above step iii (10 mmol) in 30 ml of anhydrous ethyl acetate, bromine (10 mmol) in 10 ml of anhydrous ethyl acetate was added dropwise over 30 min with stirring at room temperature. After stirring of the solution for an additional 1-2 h, the precipitates were filtered and washed with anhydrous ethyl ether. The solid was suspended in saturated sodium bicarbonate with stirring for 15 min, then filtered and washed with water. The solid was dried in vacuo. Analytically pure samples were prepared by re-crystallization from methanol or ethanol or by column chromatography.

The following compounds were obtained using the procedures described above:

3-hydroxy-5-14-(phenylamino)phenylamino]isothiazole-4-carbonitrile: 1H NMR (DMSO-d6): 9.91 (brs, 1H, OH), 8.20 (brs, 1H, NH), 8.07 (brs, 1H, NH), 7.32-7.86 (m, 9H). MS: 308.

5-14-(4-bromophenylamino)phenylamino]-3-hydro isothiazole-4-carbonitrile: $^1$H NMR (DMSO-$d_6$): 8.43 (s, 1H, NH), 7.38 (d, 2H, J=4.8 Hz), 7.20 (d, 2H, J=4.8 Hz), 7.10 (d, 2H, J=4.8 Hz), 7.01 (d, 2H, J=4.8 Hz). MS: 386, 388;

Procedures (Step v)

The typical procedure for synthesis of 3-Hydroxy-N-isopropyl-5-1-(4-phenylamino)phenylaminoPisothiazole-4-carboxamidine illustrates the general procedures of Step v. Most reactions were run by using 100-200 mg of starting materials in about 20-30 ml of ethanol at 90° C. for 24-48 hours. In most cases products were purified by silica gel column chromatography. Some compounds were purified by preparative HPLC or TLC.

A mixture of 3-Hydroxy-4-cyano-544-(phenylamino)phenylaminopsothiazole (5 g) and isopropylamine (25 ml) in 250 ml of ethanol was placed into an high-pressure reaction vessel and heated to 120° C. with stirring for 9 hours. The reaction mixture was cooled to room temperature, and the solvent was removed in vacuo. The residue was treated with 500 ml of diethyl ether, and the precipitates were filtered and washed with diethyl ether. The filtrates were evaporated to dryness and the residue was chromatographed by silica gel column (chloroform/methanol, 60:1) to give 3.51 g (59%) of product as a foam, which was recrystallized from methanol to give yellowish crystals. MS: 367; $^1$H NMR (DMSO-d6): 10.52 (brs, ½H, NH, D$_2$O exchangeable), 9.89 (brs, ½H, NH, D$_2$O exchangeable), 9.47 (brs, ½H, NH, D$_2$O exchangeable), 9.14 (brs, ½H, NH, D$_2$O exchangeable), 8.19 (s, 1H, OH, D$_2$O exchangeable), 8.01 (s, 1H, NH, D$_2$O exchangeable), 7.84 (brs, ½H, NH, D$_2$O exchangeable), 7.58 (brs, ½H, NH, D$_2$O exchangeable), 7.17 (t, 2H, J=7.5 Hz, ArH), 7.00 (d, 2H, J=8.7 Hz, ArH), 6.97 (d, 2H, J=8.7 Hz, ArH), 6.83 (d, 2H, J=8.7 Hz, ArH), 6.73 (t, 1H, J=7.5 Hz, ArH), 3.85 (m, 1H, CHN), 1.20 (d, 6H, J=6.3 Hz, 2×CH$_3$).

EXAMPLES

The following compounds were obtained by the above-described procedures of steps i-v.

5-[4-(4-Bromophenylamino)phenylaminoP3-hydroxy-N-isopropyl-isothiazole-4-carboxamidine MS: 445, 447; $^1$H NMR (DMSO-d6): 10.50 (brs, ½H, NH, D$_2$O exchangeable), 9.89 (brs, ½H, NH, D$_2$O exchangeable), 9.49 (brs, ½H, NH, D$_2$O exchangeable), 9.14 (brs, ½H, NH, D$_2$O exchangeable), 8.25 (s, 1H, NH, D$_2$O exchangeable), 8.17 (s, 1H, OH, D$_2$O exchangeable), 7.84 (brs, ½H, NH, D$_2$O exchangeable), 7.59 (brs, ½H, NH, D$_2$O exchangeable), 7.30 (d, 2H, J=8.7 Hz, ArH), 7.01 (d, 2H, J=8.7 Hz, ArH), 6.91 (d, 2H, J=8.7 Hz, ArH), 6.85 (d, 2H, J=8.7 Hz, ArH), 3.85 (m, 1H, CHN), 1.20 (d, 6H, J=6.3 Hz, 2×CH$_3$).

3-Hydroxy-N-(2-hydroxy-1-methyl-ethyl)-5-(4-phenylamino-phenylamino)-isothiazole-4-carboxamidine MS: 383; $^1$H NMR (DMSO-d6): 10.64 (brs, ½H, NH, D$_2$O exchangeable), 9.90 (brs, ½H, NH, D$_2$O exchangeable), 9.56 (brs, ½H, NH, D$_2$O exchangeable), 9.14 (brs, ½H, NH, D$_2$O exchangeable), 8.22 (s, 1H, NH, D$_2$O exchangeable), 8.00 (s, 1H, OH, D$_2$O exchangeable), 7.80 (brs, ½H, NH, D$_2$O exchangeable), 7.52 (brs, ½H, NH, D$_2$O exchangeable), 7.17 (t, 2H, J=7.5 Hz, ArH), 7.00 (d, 2H, J=8.7 Hz, ArH), 6.97 (d, 2H, J=8.7 Hz, ArH), 6.83 (d, 2H, J=8.7 Hz, ArH), 6.73 (t, 1H, J=7.5 Hz, ArH), 5.06 (t, 1H, J=4.8 Hz, OH, D$_2$O exchangeable), 3.77 (m, 1H, CHN), 3.47 (m, 1H, CH), 3.42 (m, 1H, CH), 1.15 (d, 3H, J=5.4 Hz, CH$_3$).

5-[4-(4-Bromo-phenylamino)-phenylamino 1-3-hydroxy-N-(2-hydroxy-1-methyl-ethyl)-isothicaole-4-carboxamidine MS: 461, 463; $^1$H NMR (DMSO-d6): 10.64 (brs, ½H, NH, D$_2$O exchangeable), 9.88 (brs, ½H, NH, D$_2$O exchangeable), 9.56 (brs, ½H, NH, D$_2$O exchangeable), 9.14 (brs, ½H, NH, D$_2$O exchangeable), 8.24 (s, 1H, NH, D$_2$O exchangeable), 8.17 (s, 1H, OH, D$_2$O exchangeable), 7.81 (brs, ½H, NH, D$_2$O exchangeable), 7.54 (brs, ½H, NH, D$_2$O exchangeable), 7.30 (d, 2H, J=8.7 Hz, ArH), 7.01 (d, 2H, J=8.7 Hz, ArH), 6.91 (d, 2H, J=8.7 Hz, ArH), 6.85 (d, 2H, J=8.7 Hz, ArH), 5.06 (t, 1H, J=5.1 Hz, OH, D$_2$O exchangeable), 3.78 (m, 1H, CHN), 3.47 (m, 1H, CH), 3.43 (m, 1H, CH), 1.14 (d, 3H, J=5.7 Hz, CH$_3$).

5-[4-(4-Bromo-phenylamino)-phenylamino]-3-hydroxy-N-(cyclohexylmethyl)-isothiazole-4-carboxamidine $^1$H NMR (DMSO-d6, 300 MHz): 10.63 (broad s, ½H), 9.84 (broad s, ½H), 9.64 (broad s, ½H), 9.06 (broad s, ½H), 8.23 (s, 1H), 8.01 (s, 1H), 7.83 (broad s, ½H), 7.57 (broad s, ½H), 7.31 (d, J=8.7 Hz, 1H), 7.18 (t, J=8.1 Hz, 2H), 7.00 (t, J=8.7 Hz, 3H), 6.92 (d, J=8.7 Hz, 1H), 6.84 (t, J=6.0 Hz, 1H), 6.74 (t, J=7.2 Hz, 1H), 3.13 (s, 2H), 1.76-1.54 (m, 6H), 1.28-1.00 (m, 5H). MS (EI) m/z 421 (M-1)+.

3-Hydroxy-N-(4-hydroxy-butyl)-5-(4-phenylamino-phenylamino)-isothiazole-4-carboxamidine $^1$H NMR (DMSO-d6, 300 MHz): 9.71 (broad s, 1H), 9.41 (broad s, 1H), 8.82 (broad s, 1H), 8.40 (broad s, 2H), 7.36 (d, J=8.7 Hz, 2H), 7.10 (s, 5H), 6.98 (d, J=8.7 Hz, 2H), 4.41 (t, J=6.3 Hz, 1H), 3.41 (t, J=6.3 Hz, 2H), 3.30-3.22 (m, 2H), 1.80-1.74 (m, 1H), 1.63-1.45 (m, 3H). MS (EI) m/z 397 (M-1)+.

N-Cyclohexylmethyl-3-hydroxy-5-(4-phenylamino-phenylamino)-isothiazole-4-carboxamidine $^1$H NMR (DMSO-d6, 300 MHz): 10.63 (broad s, ½H), 9.84 (broad s, ½H), 9.64 (broad s, ½H), 9.06 (broad s, ½H), 8.23 (s, 1H), 8.01 (s, 1H), 7.83 (broad s, ½H), 7.57 (broad s, ½H), 7.31 (d, J=8.7 Hz, 1H), 7.18 (t, J=8.1 Hz, 2H), 7.00 (t, J=8.7 Hz, 3H), 6.92 (d, J=8.7 Hz, 1H), 6.84 (t, J=6.0 Hz, 1H), 6.74 (t, J=7.2 Hz, 1H), 3.13 (s, 2H), 1.76-1.54 (m, 6H), 1.28-1.00 (m, 5H). MS (EI) m/z 421 (M-1)+.

Cell lines and treatments. The EBV-immortalized normal lymphoblastoid cell line LCL-N was cultured in RPMI 1640 medium supplemented with 15% heat inactivated fetal calf serum (FCS). Immortalized normal human foreskin fibroblasts BjhTERT were cultured in DMEM plus M199 (4 to 1 ratio) with 10% FCS. HCT15, HCT115-Chk2−/−, and HCT116 colon cancer cell lines were grown in DMEM and McCoy's 5A, respectively, with 10% FCS. Culture media contained penicillin (100 U/ml), streptomycin (100 µg/ml) and glutamine (2 mM). Cells were cultured at 37° C. in a 5% CO$_2$ incubator. The compound was stored at −20° C. as a 10 mM stock solution in DMSO, and diluted to a maximal final DMSO concentration of 0.1% in the reaction buffer or culture medium. An ATM kinase inhibitor was added to exponentially growing cells 1 to 2.5 hrs before irradiation in positive control experiments. Cells were irradiated with an IBL437a instrument (Oris Industries, France) equipped with a 137Cs source providing 675 cGy/min. The spectrophotometric measurement of cell viability was done using the 3-(4,5-dimethylthiazol-2-yl)-2,5-diphenyltetrazolium bromide assay (Sigma, St. Louis, Mo.) and a Tecan (Maennedorf Switzerland) 96-well plate reader.

Western blots. Untreated or treated cells were washed with PBS plus 0.1 mM Na$_3$VO$_4$ (Sigma), pelleted and lysed in Laemli buffer (0.125 M Tris-HCl, pH 6.8, 5% SDS) containing protease and phosphatase inhibitors including 1 mM phenylmethylsulfonyl fluoride (PMSF), 10 µg/ml pepstatin, 100 KIU/ml aprotinin, 10/µml leupeptin (all from Calbiochem, San Diego, Calif.), and 1 mM Na$_3$VO$_4$. After boiling for 5 min and sonicated, lysates were quantitated by micro-BCA assay (Pierce, Rockford, Ill.). Aliquotes containing 50 µg of protein plus 5% P-mercaptoethanol were size-fractionated on 5 or 8% SDS-PAGE and electroblotted onto PVDF membranes (Millipore, Bedford, Mass.). After blocking with 4% non-fat dried milk in PBS plus 0.1% Tween 20 (Sigma), membranes were incubated with monoclonal antibodies for Chk2 (clone 44D4/21) (20, 18), p53 (clone DO-7), β-actin (Sigma, Italy), vinculin (Sigma) and with rabbit antibodies specific for the phosphorylated residues of Chk2 Thr387, Thr68, Ser19, Ser33-35, of p53 Ser15 and Ser20, and of Chk1 Ser345 (all from Cell Signaling Technology, Beverly, Mass.). Rabbit antibodies against Smc1-phosphoSer966, total Smc1, Hdmx and Chk1 phospho-Ser317 were from Bethyl Laboratories, Montgomery, Tex. Binding of antibodies to membranes was detected with peroxidaseconjugated secondary antibodies and ECL Super Signal (Pierce, Rockford, Ill.) on autoradiographic films. Bands were acquired with a DuoScan system (Agfa, Mortsel, Belgium) and quantitated by ImageQuant software (Molecular Dynamics).

Chk2 immunoprecipitation and kinase assay. Cells were lysed for 30 min in ice-cold buffer containing 20 mM Tris-HCl, pH 8, 0.5% NP-40, 150 mM NaCl, 1 mM EDTA, 1 mM PMSF, pepstatin (1 µg/ml), leupeptin (2 µg/ml), aprotinin (2 µg/ml), 25 mM NaF, 1 mM EDTA, and 1 mM Na$_3$VO$_4$. After treatment with 15 µl of immobilized protein G (Sigma) for 45 min at 4° C., lysates were immunoprecipitated as described (21) with 5 µg of anti-Chk2 antibody (clone 44D4/21) and 15 µl of immobilized protein G at 4° C. for 3 hrs. The Chk2 kinase activity in the lysate was assayed at 30° C. for 30 min in a 20-µl reaction mixture containing 50 mM HEPES (pH 8.0), 10 mM MgCl$_2$, 2.5 mM EDTA, 1 mM dithiothreitol, 10 µM β-glycerophosphate, 1 mM NaF, 0.1 mM Na$_3$VO$_4$, 0.1 mM PMSF, 10 µM ATP, and 30 µCi of [γ-$^{32}$P]ATP and when required, glutathione S-transferase (GST)-Cdc25C fragment as a substrate. The reaction products were separated by SDS-PAGE, autoradiographed, and western blotted to verify the amount of immunoprecipitated Chk2 per sample.

In vitro kinase assays with recombinant Chk1 and Chk2. Recombinant human GST-Chk1 and GST-Chk2 proteins were purchased from Upstate (Lake Placid, N.Y.). Assay conditions were based on published protocols with minor modifications. Briefly, 10 nM of Chk1 or Chk2 was used to phosphorylate 25 µM myelin basic protein (MBP) (Invitrogen, Carlsbad, Calif.) This reaction took place in a buffer that contained 8 mM MOPS, pH 7.2, 10 mM β-glycerol phosphate, 1.5 mM EGTA, 0.4 mM EDTA, 0.4 mM sodium orthovanadate, 100 µM ATP, 1 µCi [γ-$^{33}$P] ATP, 15 mM MgCl$_2$, 0.4 mM DTT, 0.006% Brij-35, 1% glycerol and 0.2 mg/ml BSA in a final volume of 25 µl. The reaction was incubated for 30 minutes at 24° C. and was terminated by adding 100 µl of 1% trichloroacetic acid. The quenched solution was incubated for 5 min at room temperature to allow the protein to precipitate and then subsequently transferred to a 96-well white GF/B filter plate (Perkin Elmer, Wellesley, Mass.) using a Perkin Elmer Filtermate Universal Harvester. The filter plate was washed ten times with water and once with ethanol before completely drying. 40 µL of Microscint™ (Perkin Elmer, Wellesley, Mass.) was added to each well and the radioactivity that was incorporated into MBP was counted using a Perkin Elmer TopCount. The compound was titrated and its IC$_{50}$ values against both Chk1 and Chk2 were determined. The reported IC$_{50}$ values are the average of at least two sets of data. To determine the competitive nature of the compound with ATP, the compound concentration was varied from 0-200 nM while ATP was varied from 50-500 μM in the assays to assess the ATP effect on inhibition. Prism 4.0 software (GraphPad, San Diego Calif.) was used for the $IC_{50}$ determination and Lineweaver-Burk kinetic analysis.

To investigate the inhibition mechanism of the compound, Chk2 assays with a catalytically active recombinant GST-Chk2 were prepared by incubating for 30 min at 30° C. with 2 μg of enzyme and 1 μg of GST-Cdc25C substrate in 30 μl of kinase buffer (20 mM Tris-HCl, 75 mM KCl, 5 mM $MgCl_2$, 0.5 mM EDTA, 2 mM dithiothreitol, 50 μM ATP, and 15 μCi of [γ-$^{32}$P]ATP). The reaction products were separated by SDS-PAGE and autoradiographed. The gels were then stained with Coomassie Blue to visualize the amount of loaded substrate per lane.

Cell cycle phase analysis. Radiation-induced cell cycle phase modifications were examined by flow cytofluorimetry on propidium iodide stained cells using a FACSCalibur instrument fitted with a Cell Quest software package (Becton Dickinson, Sunnyvale, Calif.).

Results: Several compounds of the invention were assayed and $IC_{50}$ values are provided in the Table 1 below.

TABLE 1

The enzymatic $IC_{50}$ values of compounds against Chk2

| Entry | $R_1$ | $R_2$ | $IC_{50}$ | Entry | $R_2$ | $IC_{50}$ |
|---|---|---|---|---|---|---|
| 1 | isopropyl | Br | A | 7 | H | A |
| 2 | HO-isobutyl | Br | A | 8 | H | A |
| 3 | HO-ethyl | Br | A | 9 | H | B |
| 4 | cyclohexylmethyl | Br | A | 10 | H | C |
| 5 | HO-butyl | Br | A | 11 | H | C |
| 6 | HO,HO-butyl (diol) | Br | A | 12 | H | B |
| 13 | naphthylmethyl | | | | H | A |

Code:
A: $IC_{50}$ = 1 nM-500 nM;
B: $IC_{50}$ = 0.5 11 M-11.1 M;
C: $IC_{50}$ = 1 pM-2 1.t M.

What is claimed is:
1. A compound of formula III:

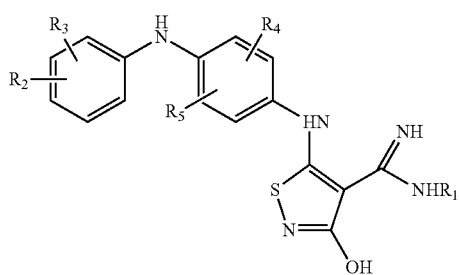

III wherein
$R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_1$ is —$CH_2$B or —$CH_2CH_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;
or $R_1$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;
or $R_1$ is —$CH(CH_2OH)CH_2D$, where D is selected from imidazolyl, indolyl, carboxamido, phenyl, cyclohexyl, —$CH_2SCH_3$, and adamantin-1-yl;

$R_2$ and $R_3$ vary independently and are selected from the group consisting of hydrogen; halogen; hydroxy; nitro; cyano; $C_1$-$C_4$ alkyl; $OC_1$-$C_4$ alkyl, where the $C_1$-$C_4$ alkyl groups and the $C_1$-$C_4$ alkyl moieties of the $OC_1$-$C_4$ alkyl groups are optionally substituted with one to three fluorine atoms; $NR_6R_7$; $(CH_3)_2N$; $CH_3OC(O)$; $CH_3CH_2OC(O)$; —C(O)$NR_6R_7$; or —$S(O)_2NR_6R_7$, where $R_6$ and $R_7$ are, independently, H, $CH_3$, or $CH_3CH_2$; or $R_2$ and $R_3$ are attached to adjacent carbons and, together with the ring atoms to which they are attached, form an additional, fused, five- or six-membered ring, optionally containing one heteroatom, which ring may be aromatic or aliphatic;

$R_4$ and $R_5$ vary independently and are selected from the group consisting of H, F, Cl, Br, $CH_3$, or $CF_3$; and salts thereof.

2. A compound of formula IV:

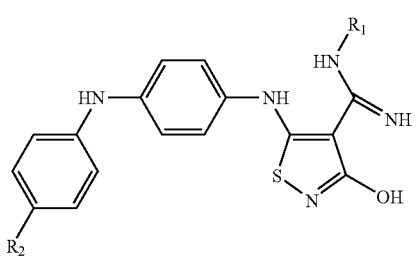

wherein
$R_1$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_1$ is —$CH_2B$ or —$CH_2CH_2B$, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or $R_1$ is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;

or $R_1$ is —$CH(CH_2OH)CH_2D$, where D is selected from imidazolyl, indolyl, carboxamido, phenyl, cyclohexyl, —$CH_2SCH_3$, and adamantin-1-yl;

$R_2$ is selected from the group consisting of hydrogen or halogen; and and salts thereof.

3. The compound of any one of claim 1 or 2, wherein $R_1$ is $C_1$-$C_6$ alkyl, optionally substituted with one or two OH groups.

4. The compound of any one of claim 1 or 2, wherein $R_1$ is —$CH_2B$, where B is selected from a $C_{3-7}$ cycloalkyl.

5. The compound of any one of claim 1 or 2, wherein or $R_1$ is —$CH_2B$ or —$CH_2CH_2B$, where B is naphthyl.

6. The compound of any one of claim 1 or 2, wherein $R_2$ is hydrogen or bromine.

7. A compound selected from the group consisting of compounds:

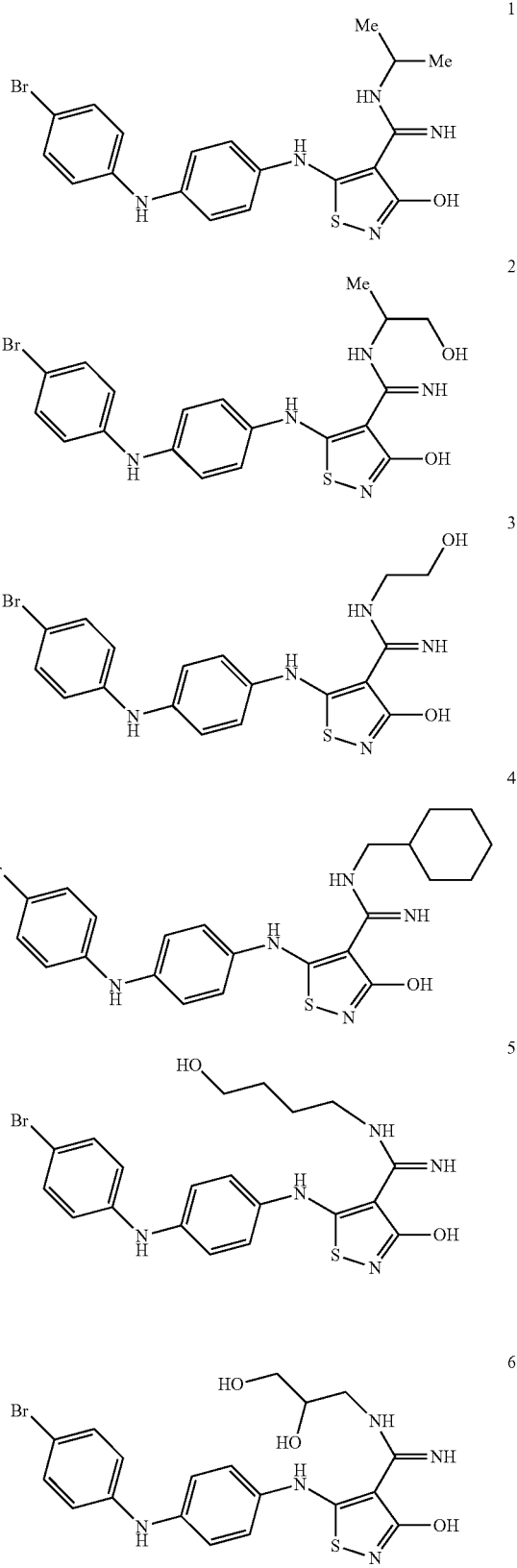

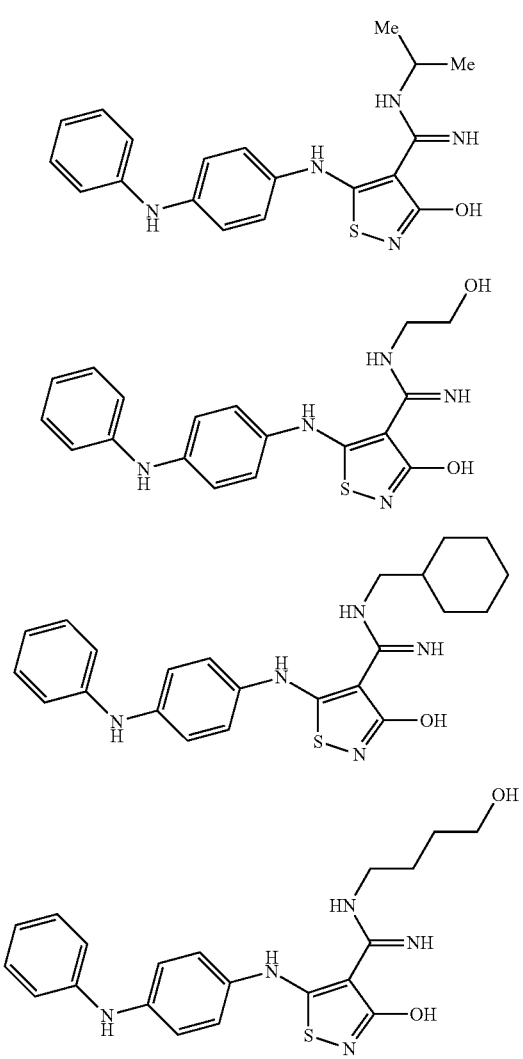

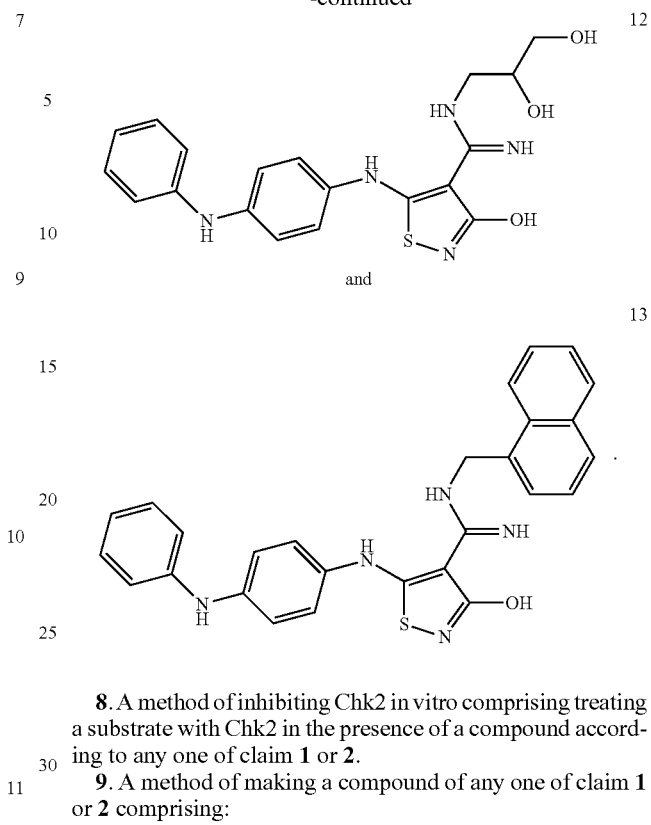

and

8. A method of inhibiting Chk2 in vitro comprising treating a substrate with Chk2 in the presence of a compound according to any one of claim 1 or 2.

9. A method of making a compound of any one of claim 1 or 2 comprising:
 a) forming a biaryl amine having an amino ($NH_2$) group;
 b) converting the amino group to an isothiocyanate group;
 c) adding a cyanoacetamide to said isothiocyanate group to form a thioamide adduct;
 d) cyclizing said thioamide adduct to form an isothiazole having a cyano group; and
 e) adding an amine to said cyano group to form a carboxamidine group.

\* \* \* \* \*